United States Patent
Bennett et al.

(10) Patent No.: US 9,422,325 B2
(45) Date of Patent: Aug. 23, 2016

(54) GLYCOSYLATION REACTIONS USING PHENYL(TRIFLUOROETHYL)IODONIUM SALTS

(71) Applicant: Trustees of Tufts College, Boston, MA (US)

(72) Inventors: Clay S. Bennett, Somerville, MA (US); An-Hsiang A. Chu, Somerville, MA (US)

(73) Assignee: Trustees of Tufts College, Boston, MA (US)

(*) Notice: Subject to any disclaimer, the term of this patent is extended or adjusted under 35 U.S.C. 154(b) by 0 days.

(21) Appl. No.: 14/505,808

(22) Filed: Oct. 3, 2014

(65) Prior Publication Data

US 2015/0099870 A1   Apr. 9, 2015

Related U.S. Application Data

(60) Provisional application No. 61/912,863, filed on Dec. 6, 2013, provisional application No. 61/886,934, filed on Oct. 4, 2013.

(51) Int. Cl.

| | | |
|---|---|---|
| C07J 17/00 | (2006.01) | |
| C07H 15/20 | (2006.01) | |
| C07H 3/06 | (2006.01) | |
| C07H 3/04 | (2006.01) | |
| C07H 1/00 | (2006.01) | |
| C07H 15/02 | (2006.01) | |
| C08B 37/00 | (2006.01) | |
| C07H 3/02 | (2006.01) | |
| C07H 15/18 | (2006.01) | |
| C07H 15/203 | (2006.01) | |
| C07J 41/00 | (2006.01) | |

(52) U.S. Cl.
CPC .............. *C07J 17/005* (2013.01); *C07H 1/00* (2013.01); *C07H 3/02* (2013.01); *C07H 3/04* (2013.01); *C07H 3/06* (2013.01); *C07H 15/18* (2013.01); *C07H 15/203* (2013.01); *C07J 41/0055* (2013.01); *C07J 41/0088* (2013.01); *C08B 37/00* (2013.01)

(58) Field of Classification Search
None
See application file for complete search history.

(56) References Cited

U.S. PATENT DOCUMENTS 7,960,554 B2    6/2011   Umemoto

OTHER PUBLICATIONS

Desmarteau, D. D. et al., "The first flouroalkylation of amino acids and peptides in water utilizing the novel iodonium salt $(CF_3SO_2)_2NI(Ph)CH_2CF_3$", *Chem. Comm.*, 20:2241-2242 (Clemson, SC, USA, 1998).

Lu, C. et al., "Fluoroalkylation of Imidazoles by Hypervalent Iodonium Salts", *Organic Letters*, 10(24):5565-5568 (USA, Oct. 17 2008).

Schmidt, R. R. et al., "Nitriles as Solvents in glycosylation Reactions: Highly Selective β- Glycoside Synthesis", *Synlett*, 11:694-696 (1990).

*Primary Examiner* — Erid Olson
*Assistant Examiner* — Bahar Craigo
(74) *Attorney, Agent, or Firm* — Dana M. Gordon; Foley Hoag LLP

(57) ABSTRACT

Provided are methods for the preparation of glycosylation products, including those represented by formula I:

Sugar-O-R'    I comprising the step of combining R'—OH, a glycosyl sulfide glycosyl donor ("thioglycoside donor"), a hypervalent iodine alkyl-transfer activating reagent, and a base. In an embodiment, the hypervalent iodine alkyl-transfer activating reagent is (phenyl(trifluoroethyl)iodonium triflimide).

23 Claims, 12 Drawing Sheets

Figure 1

| Acceptor | Donor 1 (BnO, OBn, SPh) | Donor 2 (OBn, OBn, SPh) | Donor 3 (BnO, OBn, OBn, SPh) | Donor 4 (OBn, OBn, OBn, SPh) | Donor 5 (BnO, OBn, N₃, SPh) | Donor 6 (AcO, OAc, OAc, SPh) | Donor 7 (OAc, OAc, SPh) |
|---|---|---|---|---|---|---|---|
| Cholesterol | 85% (1.3 : 1) | 68% (1.4 : 1) | w/o TTBP: 63% (1.9 : 1); with TTBP: 70.5% (1 : 1); wet DCM: 45% (1 : 1) | | w/o TTBP: 53% (1 : 1.5); with TTBP: 84% (1 : 2.2) | Donor:Acceptor 1:2 w/o TTBP 66.5% (α); Donor:Acceptor 1:2 with TTBP 72% (α); Donor:Acceptor 2:1 with TTBP 90% (α) | Donor:Acceptor 1:2 49% (α); Donor:Acceptor 1:2 87.2% (α) |
| C-3 | 90% (2.5 : 1) | 85% (1.8 : 1) | 83% (1.6 : 1) | 80% (1.7 : 1) | 72% (1 : 1.4) | Donor:Acceptor 1:2 47% (α); Donor:Acceptor 2:1 90% (α) | Donor:Acceptor 1:2 N.R.; Donor:Acceptor 2:1 N.R. |
| C-6 | 73% (1.2 : 1) | 76% (1 : 1.5) | 90% (2.7 : 1) | 90% (1.4 : 1) | 73% (1 : 2.5) | Donor:Acceptor 1:2 37% (α); Donor:Acceptor 2:1 97% (1.5 : 1) | Donor:Acceptor 1:2 11% (α); Donor:Acceptor 2:1 38% (α) |

(X : Y) : α : β anomeric ratio

Figure 3
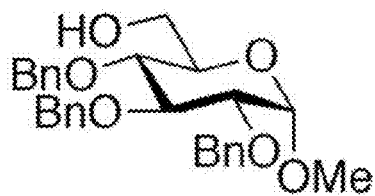
Methyl,2,3,4-tri-*O*-benzyl
-α-D-Glucopyranoside
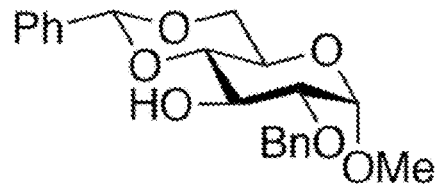
Methyl,2-*O*-benzyl-4,6-*O*-
benzylidene-α-D-glucopyranoside Figure 4
Thioglycoside Donors
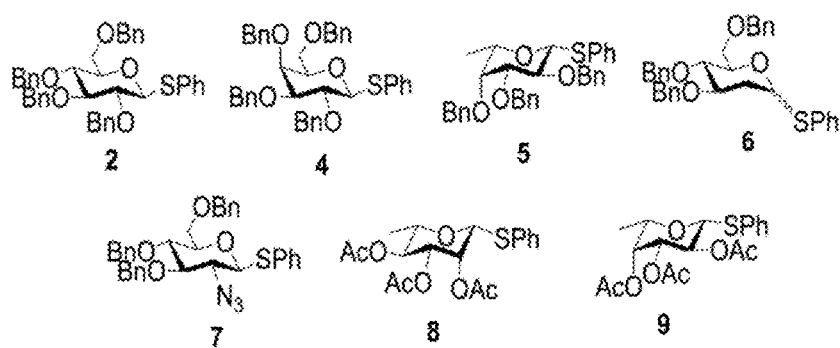
Acceptors
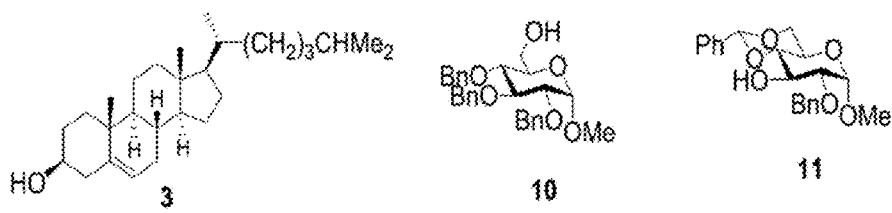

| Entry | Donor | t [h] | Base | Product | Yield [%][b] | α : β[c] |
|---|---|---|---|---|---|---|
| 1 | 2 | 0.2 | - | 12 | 63 | 1.9 : 1 |
| 2 | 2 | 24 | - | 12 | 0 | N/A |
| 3 | 2 | 1 | TTBP | 12 | 71 | 1 : 1 |
| 4 | 7 | 1.5 | - | 24 | 53 | 1 : 1.5 |
| 5 | 7 | 2.5 | TTBP | 24 | 84 | 1 : 2.2 |
| 6 | 8 | 1.5 | - | 27 | 67 | α |
| 7 | 8 | 2.5 | TTBP | 27 | 72 | α |

[a] Reaction conditions: donor (1 equiv), acceptor (2 equiv), 1 (1.2 equiv), TTBP (3 equiv), RT, CH$_2$Cl$_2$
[b] Isolated yield after silica gel flash chromotography
[c] Determined by NMR spectroscopy

| Entry | Donor | ROH | t [h] | Product | Yield [%][b] | α : β[c] |
|---|---|---|---|---|---|---|
| 1 | 2 | 3 | 1 | 12 | 71 | 1 : 1 |
| 2 | 2 | 10 | 0.2 | 13 | 90 | 2.7 : 1 |
| 3 | 2 | 11 | 1.5 | 14 | 83 | 1.6 : 1 |
| 4 | 4 | 3 | 1 | 15 | 91 | 1.3 : 1 |
| 5 | 4 | 10 | 0.2 | 16 | 90 | 1.4 : 1 |
| 6 | 4 | 11 | 0.7 | 17 | 80 | 1.7 : 1 |
| 7 | 5 | 3 | 0.5 | 18 | 68 | 1 : 1.4 |
| 8 | 5 | 10 | 0.1 | 19 | 76 | 1 : 1.5 |
| 9 | 5 | 11 | 0.1 | 20 | 85 | 1.8 : 1 |
| 10 | 6 | 3 | 3 | 21 | 85 | 1.3 : 1 |
| 11 | 6 | 10 | 1.5 | 22 | 73 | 1.2 : 1 |
| 12 | 6 | 11 | 2.5 | 23 | 90 | 2.5 : 1 |

[a] Reaction conditions: donor (1 equiv), acceptor (2 equiv), 1 (1.2 equiv), TTBP (3 equiv), RT, $CH_2Cl_2$
[b] Isolated yield after silica gel flash chromotography
[c] Determined by NMR spectroscopy

| Entry | Donor | R'OH | Donor : Acceptor | t [h] | Product | Yield [%][b] | α : β[c] |
|---|---|---|---|---|---|---|---|
| 1 | 7 | 3 | 1 : 2 | 2.5 | 24 | 84 | 1 : 2.2 |
| 2 | 7 | 10 | 1 : 2 | 2 | 25 | 73 | 1 : 2.5 |
| 3 | 7 | 11 | 1 : 2 | 3.5 | 26 | 72 | 1 : 1.4 |
| 4 | 8 | 3 | 1 : 2 | 3.5 | 27 | 72 | α |
| 5 | 8 | 3 | 2 : 1 | 3.5 | 27 | 90 | α |
| 6 | 8 | 10 | 1 : 2 | 3.5 | 28 | 37 | α |
| 7 | 8 | 10 | 2 : 1 | 3.5 | 28 | 97 | 1 : 1.5 |
| 8 | 8 | 11 | 1 : 2 | 3.5 | 29 | 47 | α |
| 9 | 8 | 11 | 2 : 1 | 3.5 | 29 | 90 | α |
| 10 | 9 | 3 | 1 : 2 | 3 | 30 | 49 | β |
| 11 | 9 | 3 | 2 : 1 | 3 | 30 | 87 | β |

[a] Reaction conditions: 1): donor (1 equiv), acceptor (2 equiv), 1 (1.2 equiv), TTBP (3 equiv); 2): donor (2 equiv), acceptor (1 equiv), 1 (2.4 equiv), TTBP (4 equiv) RT, CH$_2$Cl$_2$
[b] Isolated yield after silica gel flash chromatography
[c] Determined by NMR spectroscopy

| Entry | Donor : Acceptor | t [h] | Product | Yield [%][b] | α : β[c] |
|---|---|---|---|---|---|
| 1 | 1 : 2 | 1 | 12 | 45 | 1 : 1 |
| 2 | 2 : 1 | 1 | 12 | 55 | 1 : 1.2 |

[a] Reaction conditions: 1): donor (1 equiv), acceptor (2 equiv), 1 (1.2 equiv), TTBP (3 equiv); 2): donor (2 equiv), acceptor (1 equiv), 1 (2.4 equiv), TTBP (4 equiv) RT, CH₂Cl₂
[b] Isolated yield after silica gel flash chromatography
[c] Determined by NMR spectroscopy

| Entry | R—⁝—CN | Yield (%) | α : β |
|:-:|:-:|:-:|:-:|
| 1 | None | 91 | 1.3 : 1 |
| 2 | Me— | 75 | 1 : 5.2 |
| 3 | Et— | 81 | 1 : 5.6 |
| 4 | iPr— | 91 | 1 : 5.1 |
| 5 | tBu— | 78 | 1 : 6.4 |
| 6 | Me₃Si— | 56 | 1 : 7 |
| 7 | Cl₃C— | 81 | 1 : 1.1 |

Chol = cholesterol
TTBP = 2,4,6-tri-*tert*-butylpyrimidine

| Entry | R—CN | Yield (%) | α : β |
|---|---|---|---|
| 1 | Me— | 86 | 1 : 4.9 |
| 2 | Et— (ethyl) | 81 | 1 : 5.6 |
| 3 | iPr— | 87 | 1 : 7.5 |
| 4 | tBu— | 78 | 1 : 9 |
| 5 | Me₃Si—CH₂— | 48 | 1 : 9.6 |

Chol = cholesterol

TTBP = 2,4,6-tri-*tert*-butylpyrimidine

Figure 11
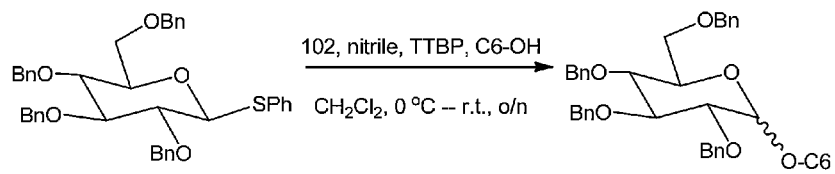
| Entry | D : A | Nitrile | Yield (%) | α : β |
|---|---|---|---|---|
| 1 | 1 : 2 | P | 46 | 1 : 10.2 |
| 2* | 1 : 2 | P | 51 | 1 : 8.5 |
| 3 | 1 : 2 | I | 55 | 1 : 6.5 |
| 4 | 2 : 1 | P | 38 | 1 : 7 |
| 5 | 1 : 2 | I + P | 68 | 1 : 12.5 |
| 6 | 1 : 2 | A + P | 77 | 1 : 10 |
| 7 | 1 : 2 | I + P + A | 70 | 1 : 25 |
*: 2.0 equiv. instead of 1.2 equiv. of promoter was used in the reaction
A = Acetonitrile
I = Isobutyronitrile
P = Pivalonitrile
Chol = cholesterol
TTBP = 2,4,6-tri-*tert*-butylpyrimidine
C6-OH = 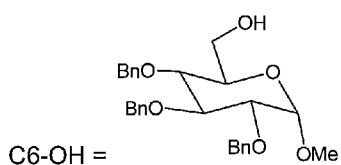

Figure 12
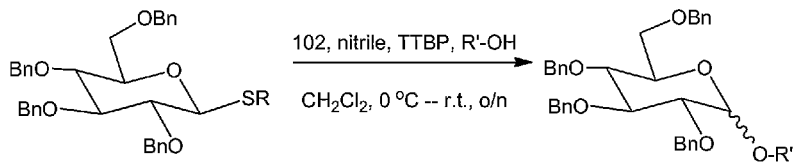
| Entry | R | Nitrile | R'-OH | Yield (%) | α : β |
|---|---|---|---|---|---|
| 1 | Ph | P | C6 | 46 | 1 : 10.4 |
| 2 | Ph | IPA | C6 | 70 | 1 : 25 |
| 3 | Ada | P | C6 | 65 | 1 : 10.7 |
| 4 | Ada | IPA | C6 | 84 | 1 : 11 |
| 5 | Ph | P | Chol | 51 | β |
| 6 | Ph | IP | Chol | 72 | 1 : 21.5 |
| 7 | Ada | P | Chol | 92 | 1 : 14 |
| 8 | Ph | P | C3 | 55 | 1 : 11.5 |
| 9 | Ada | P | C3 | 85 | 1 : 6.5 |
| 10 | Ada | IPA | C3 | 85 | 1 : 6.5 |
A = Acetonitrile; I = Isobutyronitrile; P = Pivalonitrile
Ada = 1-Adamantyl
Chol = cholesterol
TTBP = 2,4,6-tri-*tert*-butylpyrimidine
C3 = 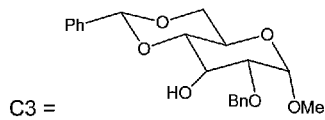
C6 = 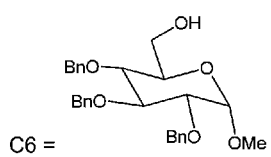

GLYCOSYLATION REACTIONS USING PHENYL(TRIFLUOROETHYL)IODONIUM SALTS

RELATED APPLICATIONS

This application claims benefit of U.S. Provisional Patent Application No. 61/886,934, filed Oct. 4, 2013; and U.S. Provisional Patent Application No. 61/912,863, filed Dec. 6, 2013.

BACKGROUND

The selective and high-yielding preparation of sugars by chemical methodology represents an ongoing challenge in organic synthesis. The usefulness of sugars, particularly oligosaccharides, is unquestioned, among whose applications are vaccines, antibiotics, molecular recognition, and other medical therapy. Chemical glycosylation reactions enable the coupling reaction of a glycosyl donor to a glycosyl acceptor to form an (oftentimes non-naturally occurring) glycoside. If both the donor and acceptor are sugars, then the product is an oligosaccharide. The reaction requires activation with a suitable activating reagent. The reactions often result in a mixture of products due to the creation of a new stereogenic center at the anomeric position of the glycosyl donor. The formation of a glycosidic linkage allows for the synthesis of complex polysaccharides which may play important roles in biological processes and pathogenesis and therefore having synthetic analogs of these molecules allows researchers to answer persistent questions in diverse scientific disciplines.

A glycosyl donor is a sugar with a suitable leaving group at the anomeric position. This group undergoes activation under the reaction conditions and is eliminated or displaced either before or after the formation of a new chemical bond between donor and acceptor. The leaving group is typically a halogen, thioether, or trichloroacetimidate.

A glycosyl acceptor is any group capable of forming a bond with the anomeric carbon atom of the glycosyl donor. Oftentimes it is a sugar with an unprotected nucleophilic hydroxyl group which may attack the anomeric carbon of the oxocarbenium ion formed during the reaction and allow for the formation of the glycosidic bond.

An activator is commonly a Lewis acid which enables the leaving group at the anomeric position to leave and results in the formation of the oxocarbenium ion.

In practice, glycosylation reactions are limited in terms of substrate scope, yield, and selectivity. Therefore, a tremendous need exists for new glycosylation methods that overcome ongoing problems in this research area, including new activation agents and leaving groups.

SUMMARY OF THE INVENTION

An aspect of the invention is a method for the preparation of glycosylation products, including those represented by formula I:

$$\text{Sugar-O—R'} \qquad \qquad \text{I}$$

comprising the step of combining R'—OH, a glycosyl donor, an activating reagent, and a base.

In an embodiment, the method comprises the step of combining R'—OH, a glycosyl donor of formula II, a reagent of formula III, and a base;

wherein said base is selected from the group consisting of pyridine, pyrimidine, 2,6-lutidine, 2,6-di-tert-butylpyridine, 2,4,6-trimethylpyridine (collidine), diisopropylethylamine (DIPEA), 1,4-diazabicyclo[2.2.2]octane (DABCO), 1,8-Bis(dimethylamino)naphthalene (Proton Sponge), 1,8-diazabicyclo[5.4.0]undec-7-ene (DBU), and 2,4,6-tri-tert-butylpyrimidine (TTBP);

Sugar is an optionally protected monosaccharide or oligosaccharide;

O is an oxygen atom attached to an anomeric carbon atom of Sugar;

R' is selected from the group consisting of alkyl, haloalkyl, cycloalkyl, alkenyl, alkynyl, aryl, heteroaryl, aralkyl, heteroaralkyl, and heterocyclyl; or R'—OH is a steroid or an optionally protected monosaccharide, disaccharide, trisaccharide, tetrasaccharide, pentasaccharide, or hexasaccharide, wherein O is not bonded to an anomeric carbon atom of R;

formula II is represented by:

$$\text{Sugar-S—R}^1 \qquad \qquad \text{II}$$

wherein

S is a sulfur atom attached to the anomeric carbon atom of Sugar;

$R^1$ is a phenyl, naphthyl, ethyl, or adamantyl group, each optionally substituted with one or more substituents independently selected from the group consisting of halo, alkyl, haloalkyl, perhaloalkyl, alkoxy, and cyano;

formula III is represented by:

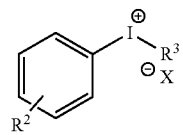

III wherein $R^2$ is absent or represents one, two, or three substituents each independently selected from the group consisting of halo, alkyl, fluoroalkyl, perfluoroalkyl, alkoxy, cyano, acyl, and acyloxy;

$R^3$ is selected from the group consisting of fluoroalkyl, fluorohaloalkyl, and perfluoroalkyl; and $X^-$ is selected from the group consisting of boron tetrafluoride, tetraarylborate, tetra(fluoroaryl)borate, hexafluoroarsenate, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogen sulfate, alkyl sulfate, aryl sulfate, carbonate, bicarbonate, carboxylate, phosphate, hydrogen phosphate, and dihydrogen phosphate;

thereby forming the compound of formula I.

The presently described methods are improved over previous methods for producing the same or similar compounds. The methods are mild, safe, reproducible, and produce few byproducts. In certain embodiments, the glycosylation method is represented by Scheme 1.

Scheme 1.

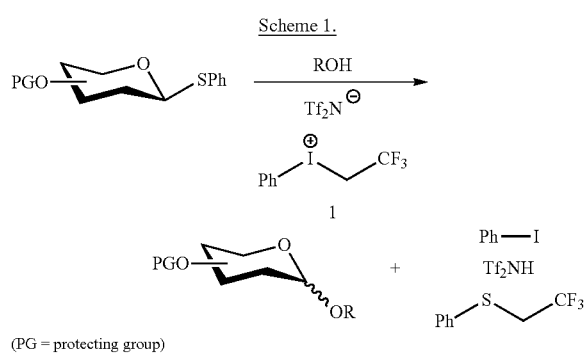

(PG = protecting group)

BRIEF DESCRIPTION OF THE DRAWINGS

FIG. 1 is a table of the results of various glycosylation reactions of the presently described method. In this Figure, "C-3" refers to methyl 2-O-benzyl-4,6-O-benzylidene-α-D-glucopyranoside. "C-6" refers to methyl 2,3,4-tri-O-benzyl-α-D-glucopyranoside. TTBP, 2,4,6-tri-tert-butylpyrimidine; DCM, dichloromethane.

FIG. 3 shows the structures of the "C-3" and "C-6" glycosyl acceptors mentioned in FIG. 1. "C-3" refers to methyl 2-O-benzyl-4,6-O-benzylidene-α-D-glucopyranoside. "C-6" refers to methyl 2,3,4-tri-O-benzyl-α-D-glucopyranoside.

FIG. 4 shows the structures of exemplary thioglycoside donors and nucleophilic acceptors useful in the present invention.

FIG. 11 tabulates the ratios of the anomeric configurations of the products obtained in glycosylations of "C6" conducted at 0° C. as a function of the identity of a nitrile additive.

FIG. 12 tabulates the ratios of the anomeric configurations of the products obtained in glycosylations conducted at 0° C. as a function of the alcohol used as the glycosyl acceptor.

DETAILED DESCRIPTION

Figure 2:
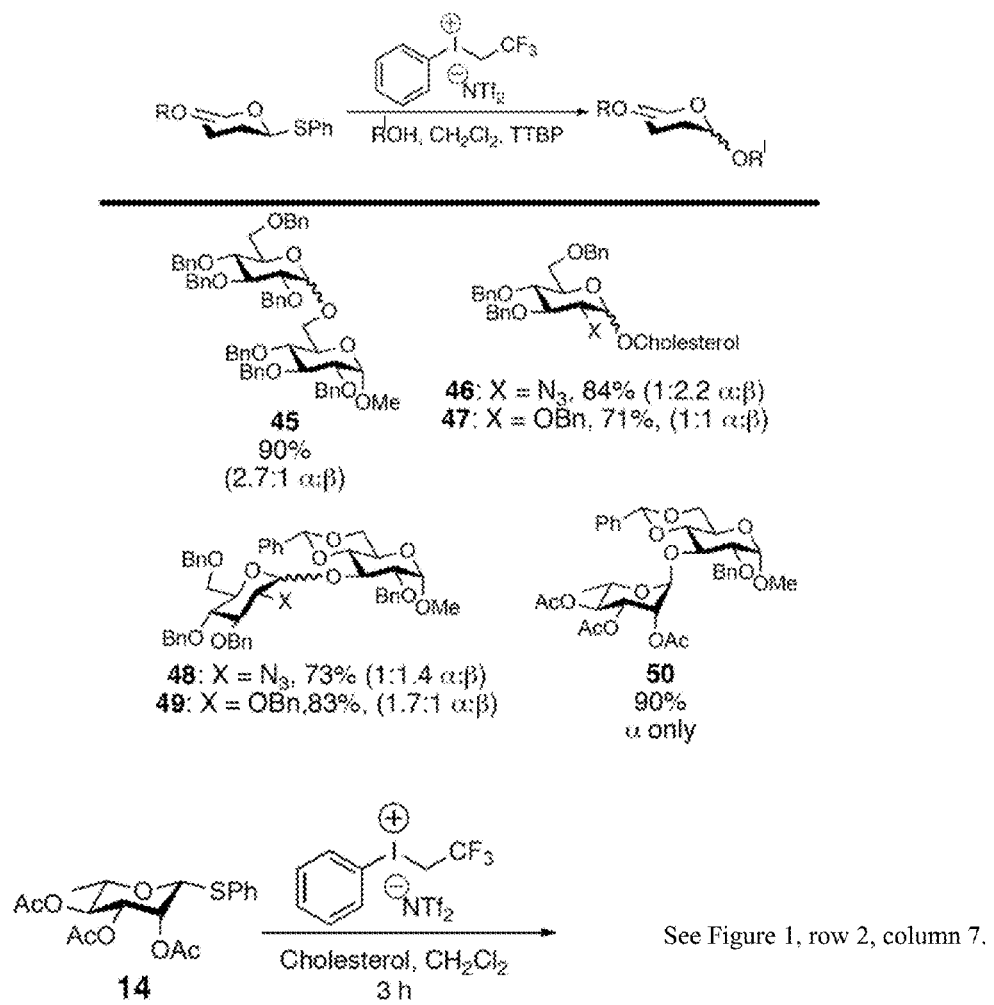
FIG. 2 shows a general reaction scheme for the present glycosylation method together with the chemical structures of several products prepared by the method (top); and the reaction of a specific glycosyl donor with cholesterol (bottom).

The use of alkylated hypervalent iodine reagents as activators in glycosylation reactions is advantageous for a number of reasons. Such reagents are generally stable, non-toxic, and relatively inexpensive. They are less powerful alkylating agents than alkyl iodides or other electrophilic alkylating agents, and therefore more selective for desired S-alkylation.

In the context of the present invention, it was discovered that hypervalent iodine alkyl-transfer reagents provide the optimal balance of reactivity and selectivity to function as highly effective activation agents. When paired with glycosyl donors bearing a thioether group, the system provides a novel and effective glycosylating platform.

A number of abbreviations and terms are used in this application. Explanations and definitions of these appear below.

As used herein, compounds which are "commercially available" may be obtained from standard commercial sources including Acros Organics (Pittsburgh, Pa.), Aldrich Chemical (Milwaukee, Wis., including Sigma Chemical and Fluka), Apin Chemicals Ltd. (Milton Park, U.K.), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hannover, Germany), Spectrum Quality Product, Inc. (New Brunswick, N.J.), TCI America (Portland, Oreg.), Trans World Chemicals, Inc. (Rockville, Md.), Wako Chemicals USA, Inc. (Richmond, Va.); Molecular Probes (Eugene, Oreg.); Applied Biosystems, Inc. (Foster City, Calif.); and Glen Research (Sterling, Va.).

As used herein, "suitable conditions" for carrying out a synthetic step are explicitly provided herein, or may be discerned by reference to publications directed to methods used in synthetic organic chemistry, or are generally known to one of ordinary skill in the art. The reference books and detailed description set forth below that describe the synthesis of intermediates useful in the preparation of compounds of the present invention will also provide suitable conditions for carrying out a synthetic step according to the present invention.

As used herein, "methods known to one of ordinary skill in the art" may be identified through various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandier et al., "Organic Functional Group Preparations", 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and/or formulation into an efficacious therapeutic agent.

"Optional" or "optionally" means that the subsequently described event or circumstances may or may not occur, and that the description includes instances where said event or circumstances occur and instances in which they do not. For example, "optionally substituted aryl" means that the aryl radical may or may not be substituted and that the description includes both substituted aryl radicals and aryl radicals having no substitution.

The term "base" as used herein may include any inorganic or organic base selected from those mentioned above in addition to non-pharmaceutically acceptable bases that are efficacious in organic chemistry. Particularly preferred organic bases are isopropylamine, diethylamine, ethanolamine, trimethylamine, dicyclohexylamine, pyridine, pyrimidine, 2,6-lutidine, 2,6-di-tert-butylpyridine, 2,4,6-trimethylpyridine (collidine), diisopropylethylamine (DIPEA), 1,4-diazabicyclo[2.2.2]octane (DABCO), 1,8-Bis(dimethylamino)naphthalene (Proton Sponge), 1,8-diazabicyclo[5.4.0]undec-7-ene (DBU), and 2,4,6-tri-tert-butylpyrimidine (TTBP).

The term "anomeric carbon atom" as used herein refers to the hemiacetal or hemiketal carbon atom of a sugar. Put simply, the anomeric carbon is the carbonyl carbon, for example a ketone or aldehyde functional group, in a carbohydrate molecule that is in its linear chain form.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "alkyl" as used herein is intended to include linear, branched, or cyclic hydrocarbon structures and combinations thereof. The term "lower alkyl" will be used herein as known in the art to refer to an alkyl, straight, branched or cyclic, of from about 1 to 6 carbons. Examples of lower alkyl groups include methyl, ethyl, propyl, isopropyl, butyl, s- and t-butyl and the like. Preferred alkyl groups are those of $C_{20}$ or below. More preferred alkyl groups are those of $C_{12}$ or below. Cycloalkyl is a subset of alkyl and includes cyclic hydrocarbon groups of from 3 to 12 carbon atoms. Examples of cycloalkyl groups include c-propyl, c-butyl, c-pentyl, norbornyl, adamantyl and the like. The terms "alkenyl" and "alkynyl" have identical chain lengths as mentioned above for "alkyl", but have one or more double or triple bonds in the carbon chain or at the two terminal positions of the carbon chain, respectively. Alkylene refers to the same residues as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower alkoxy refers to groups containing one to four carbons.

Acyl refers to groups of from 1 to 8 carbon atoms of a straight, branched or cyclic configuration, or a combination of any such configurations, attached to the parent structure through a carbonyl functionality. Such acyl groups can be saturated or unsaturated, and aromatic or non-aromatic. One or more carbons in the acyl residue can be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower acyl refers to groups containing one to four carbons.

Aryl means a 5- or 6-membered aromatic ring; a bicyclic 9- or 10-membered aromatic ring system; or a tricyclic 13- or 14-membered aromatic ring system. The aromatic 6- to 14-membered carbocyclic rings include, e.g., benzene, naphthalene, indane, tetralin, and fluorene.

Heteroaryl means a 5- or 6-membered heteroaromatic ring containing 0-3 heteroatoms selected from O, N, or S; a bicyclic 9- or 10-membered heteroaromatic ring system containing 0-3 heteroatoms selected from O, N, or S; or a tricyclic 13- or 14-membered heteroaromatic ring system containing 0-3 heteroatoms selected from O, N, or S. The 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Aralkyl refers to a residue in which an aryl moiety is attached to the parent structure via an alkyl residue. Examples are benzyl, phenethyl, phenylvinyl, phenylallyl and the like. Oxaalkyl and oxaalkylaryl refer to alkyl and alkylaryl residues in which one or more methylenes have been replaced by oxygen. Examples of oxaalkyl and oxaalkylaryl residues are ethoxyethoxyethyl (3,6-dioxaoctyl), benzyloxymethyl and phenoxymethyl; in general, glycol ethers, such as polyethyleneglycol, are intended to be encompassed by this group. Heteroaralkyl refers to a residue in which a heteroaryl moiety is attached to the parent structure via an alkyl residue. Examples include furanylmethyl, pyridinylmethyl, pyrimidinylethyl and the like.

Oxaalkyl and oxaalkylaryl refer to alkyl and alkylaryl residues in which one or more methylenes have been replaced by oxygen. Examples of oxaalkyl and oxaalkylaryl residues are ethoxyethoxyethyl(3,6-dioxaoctyl), benzyloxymethyl and phenoxymethyl; in general, glycol ethers, such as polyethyleneglycol, are intended to be encompassed by this group.

Heterocyclyl means a cycloalkyl or aryl residue in which one to four of the carbons is replaced by a heteroatom such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. "N-heterocyclyl" refers to a nitrogen-containing heterocycle as a substituent residue. The term heterocyclyl encompasses heteroaryl, which is a subset of heterocyclyl. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

Substituted alkyl, aryl and heteroaryl refer to alkyl, aryl or heteroaryl wherein one or more hydrogen atom(s) is replaced with alkyl, halogen, hydroxy, alkoxy, alkylenedioxy (e.g. methylenedioxy) fluoroalkyl, carboxy (—COOH), carboalkoxy (i.e. acyloxy RCOO—), carboxyalkyl (—COOR), carboxamido, sulfonamidoalkyl, sulfonamidoaryl, aminocarbonyl, benzyloxycarbonylamino (CBZ-amino), cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, substituted heterocyclyl, phenoxy, benzyloxy, or heteroaryloxy. For the purposes of the present invention, substituted alkyl also includes oxaalkyl residues, i.e. alkyl residues in which one or more carbons has been replaced by oxygen. Preferred substitutions include alkyl, alkenyl, alkynyl, halogen, hydroxy, alkoxy, fluoroalkyl, cyano, carbonyl, nitro, dialkylamino, alkylamino, amino, alkylthio, aralkyl, heteroaryl, and heterocyclyl.

Halogen refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

As used herein, the term "monosaccharide" refers to a simple sugar of the formula $(CH_2O)_n$. The monosaccharides can be straight-chain or ring systems, and can include a saccharose unit of the formula —CH(OH)—C(=O)—. Examples of monosaccharides include erythrose, threose, ribose, arabinose, xylose, lyxose, allose, altrose, glucose, mannose, gulose, idose, galactose, talose, erythulose, ribulose, xylulose, psicose, fructose, sorbose, tagatose, erythropentulose, threopentulose, glycerotetrulose, glucopyranose, fructofuranose. In certain embodiments, the monosaccharide is a pyranoside. In certain embodiments, the monosaccharide is a glucopyranose. In certain embodiments, the monosaccharide is a furanoside.

As used herein, the term "disaccharide" refers to two monosaccharide units joined together by a chemical bond. The terms "trisaccharide", "tetrasaccharide", "pentasaccharide", and "hexasaccharide" refer to chains of 3, 4, 5, and 6 monosaccharide units, respectively, joined together by a chemical bond. In certain embodiments, each residue of the saccharide is a pyranoside. In certain embodiments, each residue of the saccharide is a furanoside. In certain embodiments, the saccharide comprises at least one pyranoside; and at least one furanoside.

As used herein, the term "oligosaccharide" refers to saccharide consisting of at least two, up to 10 glycosidically linked monosaccharide units, preferably of 2 to 8 monosaccharide units, more preferably of 2 to 7 monosaccharide units, and even more preferably of 2 to 6 monosaccharide units or of 2 to 5 monosaccharide units. In certain embodiments, each residue of the saccharide is a pyranoside. In certain embodiments, each residue of the saccharide is a furanoside. In certain embodiments, the saccharide comprises at least one pyranoside; and at least one furanoside.

The terms "solvent", "inert organic solvent" or "inert solvent" mean a solvent inert under the conditions of the reaction being described in conjunction therewith. Solvents employed in synthesis of the compounds of the invention include, for example, methanol, acetone, water, acetonitrile, isobutyronitrile, pivalonitrile, benzonitrile, 1,4-dioxane, dimethylformamide, benzene, toluene, tetrahydrofuran, chloroform, methylene chloride (or dichloromethane), diethyl ether, tert-butyl methyl ether (TBME), pyridine and the like, as well as mixtures thereof. Unless specified to the contrary, the solvents used in the reactions of the present invention are inert organic solvents.

As used herein, the term "amino" means —NH$_2$; as well as a moiety that can be represented by the general formula:

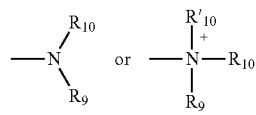

wherein $R_9$, $R_{10}$ and $R'_{10}$ each independently represent a group permitted by the rules of valence.

As used herein, the term "hydroxyl" means —OH.

As used herein, the term "nitro" means —NO$_2$.

As used herein, the term "thiol" means —SH.

As used herein, the term "sulfonyl" means —SO$_2$—.

As used herein, the term "disulfide" refers to any chemical compound that comprises a covalently linked pair of sulfur atoms (disulfide bond), e.g., diphenyl disulfide ($C_6H_5$—S—S—$C_6H_5$).

The terms "amine" and "amino" are art-recognized and refer to both unsubstituted and substituted amines, e.g., a moiety that can be represented by the general formula:

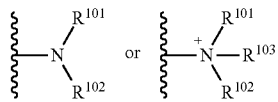

wherein $R^{101}$, $R^{102}$ and $R^{103}$ each independently represent hydrogen, alkyl, alkenyl, alkynyl, aryl, heteroaryl, —(CH$_2$)$_m$R$^{200}$, wherein m is an integer 1-10 and $R^{200}$ represents a group permitted by the rules of valence, such as hydrogen, alkyl, alkenyl, alkynyl, aryl, and heteroaryl.

The term "amino" also includes "acylamino," which is art-recognized and refers to a moiety that can be represented by the general formula:

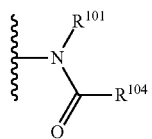

wherein $R^{101}$ is as defined above, and $R^{104}$ represents hydrogen, alkyl, alkenyl, alkynyl, aryl, heteroaryl or —(CH$_2$)$_m$R$^{200}$, wherein m and $R^{200}$ are defined above.

The term "amido" is art-recognized as an amino-substituted carbonyl and includes a moiety that can be represented by the general formula:

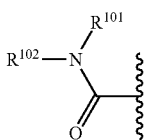

wherein $R^{101}$ and $R^{102}$ are as defined above. Preferred embodiments of the amide will not include those which are unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R^{200}$, wherein m and $R^{200}$ are defined above. Representative alkylthio groups include methylthio and ethylthio.

The term "carbonyl" is art-recognized and includes such moieties as can be represented by the general formula:

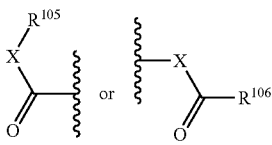

wherein X is a bond or represents an oxygen or a sulfur, and $R^{105}$ represents a hydrogen, alkyl, alkenyl, alkynyl, aryl, heteroaryl or —$(CH_2)_m R^{200}$, wherein m and $R^{200}$ are defined above, or a pharmaceutically acceptable salt, and $R^{106}$ represents hydrogen, alkyl, alkenyl, alkynyl, aryl, heteroaryl or —$(CH_2)_m R^{200}$, wherein m and $R^{200}$ are defined above. Where X is oxygen and $R^{105}$ or $R^{106}$ is not hydrogen, the formula represents an "ester". Where X is oxygen and $R^{105}$ is as defined above, the moiety is referred to herein as a carboxyl group, and particularly when $R^{105}$ is hydrogen, the formula represents a "carboxylic acid". Where X is oxygen and $R^{106}$ is hydrogen, the formula represents a "formate". In general, where the oxygen atom of the above formula is replaced by sulfur, the formula represents a "thiocarbonyl" group. Where X is a sulfur and $R^{105}$ or $R^{106}$ is not hydrogen, the formula represents a "thioester." Where X is sulfur and $R^{105}$ is hydrogen, the formula represents a "thiolcarboxylic acid." Where X is a sulfur and $R^{106}$ is hydrogen, the formula represents a "thiolformate." On the other hand, where X is a bond and $R^{105}$ is not hydrogen, the above formula represents a "ketone" group. Where X is a bond, and $R^{106}$ is hydrogen, the above formula represents an "aldehyde" group.

The terms "alkoxyl" or "alkoxy" as used herein refer to an alkyl group, as defined above, having an oxygen radical attached thereto. Representative alkoxyl groups include methoxy, ethoxy, propyloxy, t-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, and —$(CH_2)_m$—$R^{200}$, where m and $R^{200}$ are as defined above.

The term "heteroatom" as used herein means an atom of any element other than carbon or hydrogen. Preferred heteroatoms are nitrogen, oxygen, sulfur, phosphorus and selenium. In one embodiment, a heteroatom is selected from nitrogen, oxygen, and sulfur. In one embodiment, a heteroatom is selected from nitrogen and oxygen. In one embodiment, a heteroatom is nitrogen. In one embodiment, a heteroatom is oxygen.

Unless otherwise specified, the reactions described herein take place at atmospheric pressure, generally within a temperature range from about −78° C. to about 200° C. In certain embodiments, the reactions described herein take place at atmospheric pressure, generally within a temperature range from about −10° C. to about 200° C. Further, unless otherwise specified, the reaction times and conditions are intended to be approximate, e.g., taking place at about atmospheric pressure within a temperature range of about −10° C. to about 200° C. over a period of about 1 to about 24 hours.

The isolation and purification procedures described herein can be effected, if desired, by any suitable separation or purification procedure such as, for example, filtration, extraction, crystallization, column chromatography, thin-layer chromatography or preparative chromatography, or a combination of these procedures. Specific illustrations of suitable separation and isolation procedures can be had by reference to the examples below. However, other equivalent separation or isolation procedures can, of course, also be used.

An aspect of the invention is a method of preparing a compound represented by formula I:

Sugar-O—R'  I comprising the step of combining R'—OH, a glycosyl donor of formula II, a reagent of formula III, and a base; wherein said base is selected from the group consisting of pyridine, pyrimidine, 2,6-lutidine, 2,6-di-tert-butylpyridine, 2,4,6-trimethylpyridine (collidine), diisopropylethylamine (DIPEA), 1,4-diazabicyclo[2.2.2]octane (DABCO), 1,8-Bis(dimethylamino)naphthalene (Proton Sponge), 1,8-diazabicyclo[5.4.0]undec-7-ene (DBU), and 2,4,6-tri-tert-butylpyrimidine (TTBP);

Sugar is an optionally protected monosaccharide or oligosaccharide;

O is an oxygen atom attached to an anomeric carbon atom of Sugar;

R' is selected from the group consisting of alkyl, haloalkyl, cycloalkyl, alkenyl, alkynyl, aryl, heteroaryl, aralkyl, heteroaralkyl, and heterocyclyl; or R'—OH is a steroid or an optionally protected monosaccharide, disaccharide, trisaccharide, tetrasaccharide, pentasaccharide, or hexasaccharide, wherein o is not bonded to an anomeric carbon atom of R;

formula II is represented by:

Sugar-S—$R^1$  II wherein

S is a sulfur atom attached to the anomeric carbon atom of Sugar;

$R^1$ is a phenyl, naphthyl, ethyl, or adamantyl group, each optionally substituted with one or more substituents independently selected from the group consisting of halo, alkyl, haloalkyl, perhaloalkyl, alkoxy, and cyano;

formula III is represented by:

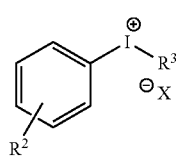

wherein
R² is absent or represents one, two, or three substituents each independently selected from the group consisting of halo, alkyl, fluoroalkyl, perfluoroalkyl, alkoxy, cyano, acyl, and acyloxy;
R³ is selected from the group consisting of fluoroalkyl, fluorohaloalkyl, and perfluoroalkyl; and
X⁻ is selected from the group consisting of boron tetrafluoride, tetraarylborate, tetra(fluoroaryl)borate, hexafluoroarsenate, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogen sulfate, alkyl sulfate, aryl sulfate, carbonate, bicarbonate, carboxylate, phosphate, hydrogen phosphate, and dihydrogen phosphate;
thereby forming the compound of formula I.

In certain embodiments, Sugar is an optionally protected monosaccharide, disaccharide, trisaccharide, tetrasaccharide, pentasaccharide, or hexasaccharide.

In certain embodiments, Sugar is an optionally protected monosaccharide, disaccharide, or trisaccharide.

In certain embodiments, Sugar is an optionally protected monosaccharide.

In certain embodiments, Sugar is a protected glucopyranoside.

In certain embodiments, R' is selected from the group consisting of alkyl, cycloalkyl, alkenyl, alkynyl, aralkyl, and heteroaralkyl; or R'—OH is a steroid or an optionally protected monosaccharide, disaccharide, trisaccharide, or tetrasaccharide.

In certain embodiments, R'—OH is cholesterol.

In certain embodiments, R'—OH is a protected monosaccharide or disaccharide.

In certain embodiments, the OH group of R'—OH that forms a bond to the anomeric carbon atom of Sugar is the C3 or C6 hydroxyl of a protected monosaccharide or disaccharide.

In certain embodiments, R'—OH is selected from the group consisting of

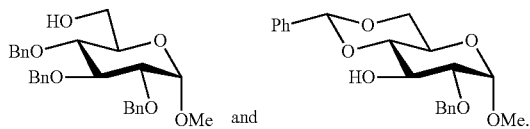

In certain embodiments, R¹ is a phenyl or naphthyl group, each optionally substituted with one halo, alkyl, or haloalkyl.

In certain embodiments, R¹ is an unsubstituted phenyl group.

In certain embodiments, R¹ is an ethyl group.
In certain embodiments, R¹ is an adamantyl group.

In certain embodiments, R² represents one or two substituents each independently selected from the group consisting of halo, alkyl, fluoroalkyl, and perfluoroalkyl.

In certain embodiments, R² is absent.

In certain embodiments, R³ is fluoroalkyl.

In certain embodiments, R³ is 2,2,2-trifluoroethyl.

In certain embodiments, X⁻ is selected from the group consisting of methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, (trifluoromethanesulfonyl) (trifluoroacetyl) amide, and bis(p-toluenesulfonyl)amide.

In certain embodiments, X⁻ is selected from the group consisting of bis(methanesulfonyl)amide, bis(trifluoromethanesulfonyl)amide, bis(benzenesulfonyl)amide, and bis(p-toluenesulfonyl)amide.

In certain embodiments, X⁻ is bis(trifluoromethanesulfonyl)amide.

In certain embodiments, the base is selected from the group consisting of pyridine, pyrimidine, 2,6-lutidine, 2,6-di-tert-butylpyridine, 2,4,6-trimethylpyridine (collidine), and 2,4,6-tri-tert-butylpyrimidine (TTBP).

In certain embodiments, the base is 2,4,6-tri-tert-butylpyrimidine (TTBP).

In certain embodiments, the glycosyl donor is selected from the group consisting of

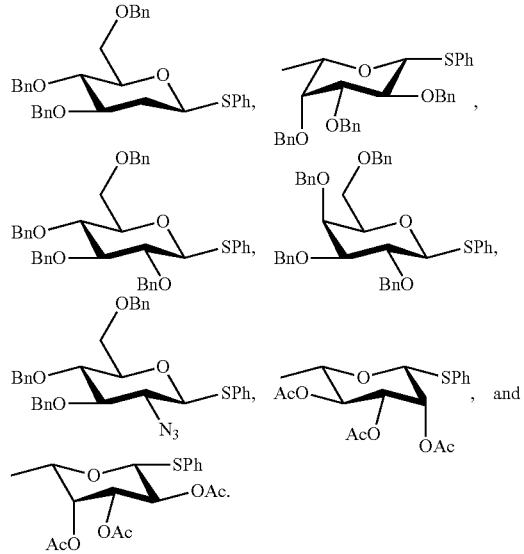

In certain embodiments, the reagent of formula III is

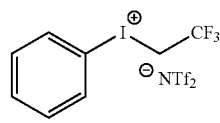

(phenyl(trifluoroethyl)iodonium triflimide).

In certain embodiments, Sugar is protected with one or more benzyl, para-methoxybenzyl, benzylidine, acetonide, methyl, acetyl, tert-butyloxycarbonyl, or silyl groups.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXEMPLIFICATION

The invention now being generally described, it will be more readily understood by reference to the following, which is included merely for purposes of illustration of certain aspects and embodiments of the present invention, and is not intended to limit the invention.

EXAMPLE 1

General Experimental Details

Procedure for Glycosylation Reactions

General Experimental Details. All reactions were performed under inert argon atmosphere. Flash column chromatography was performed on SiliCycle P-60 silica gel, 230-400 mesh. Analytical and preparative thin layer chromatography was carried out on EMD silica gel 60 F-254 plates. Products were visualized using UV or by staining with 5% aqueous sulfuric acid or ceric ammonium molybdate. NMR spectra were recorded on a Bruker Avance III NMR spectrometer at 500 MHz for $^1$H NMR and 125 MHz for $^{13}$C NMR. NMR data are reported as follows: δ shift, multiplicity [s=singlet, m=multiplet, t=triplet, d=doublet, dd=doublet of doublets, ddd=doublet of doublet of doublets, dddd=doublet of doublet of doublet of doublets, dt=doublet of triplets, td=triplet of doublets, q=quartet], coupling constants are reported in Hz. Low resolution mass spectra (LRMS) were recorded using a Finnigan LTQ ESI-MS with an additional APCI source. High resolution mass spectra (HRMS) were obtained at Massachusetts Institute of Technology Department of Chemistry instrumentation facility using a peak-matching protocol to determine the mass and error range of the molecular ion. Optical rotations were measured on a Rudolph Research Analysis AUTOPUL IV polarimeter at 589 nm in a 5 cm cell at 24° C.

Materials. Prior to running the glycosylation reactions, starting materials were dried by repeated azeotropic removal of water using toluene and a rotary evaporator at <40° C. Solvents for reactions were dried on an Innovative Technologies PureSolv 400 solvent purifier. NMR solvents were purchased from Cambridge Isotope Labs.

General Glycosylation Procedure. To a stirring solution of glycosyl donor (0.079 mmol), glycosyl acceptor (0.158 mmoles), and 2,4,6-tert-butylpyrimidine (TTBP, 0.158 mmol) in 2 mL dry dichloromethane was added phenyl(trifluoroethyl)iodonium triflimide (0.095 mmol) in 2 mL of dry dichloromethane dropwise at room temperature. Once thin layer chromatography indicated that the reaction was complete (typically 10 min to 3.5 h), it was quenched with 0.1 ml of triethylamine (Et$_3$N) and concentrated in vacuo. Flash column chromatography afforded the desired product as determined by $^1$H and $^{13}$C NMR.

EXAMPLE 2

Results of Glycosylations with Armed and Unarmed Donors

Thioglycosides have become popular glycosyl donors due to their ease of preparation and stability towards a wide range of conditions. Modulating the reactivity of either the glycosyl donor or the thiol aglycone permits the use of thioglycosides in one-pot and iterative oligosaccharide synthesis. Importantly, the use of pre-activation protocols also allows the use of thioglycosides with similar reactivity in one-pot synthesis. In addition, a number of thiophilic promoter systems have been demonstrated to activate thioglycoside donors for a subsequent glycosylation.

Nevertheless, several issues prevent the chemical biology community from broadly adopting this chemistry. In particular, many thiophilic promoter systems require the use of toxic reagents, extremely low reaction temperatures (−78° C., or lower), and/or unstable reagents that must be purified before each glycosylation reaction. Collectively, these factors present a significant barrier that prevents laboratories with limited synthetic capabilities from utilizing carbohydrate synthesis as a tool to aid in the study of glycobiology.

Phenyl(trifluoroethyl)iodonium triflimide ([(CF$_3$SO$_2$)$_2$N]I (Ph)CH$_2$CF$_3$, 1) functions as a water- and air-stable thiophilic glycosylation promoter. The iodonium salt is known to alkylate nucleophiles, including moderately reactive alpha-amino acids, even under aqueous conditions, displaying a synergy of high reactivity and robustness. Moreover, iodonium salts with up to 10-carbon fluoroalkyl chains, which are potent fluoroalkylating agents but somewhat less reactive than 1, alkylate the thioether of methionine even under solid-phase peptide synthesis (SPPS) conditions, where nucleophilic functional groups are less accessible and at times recalcitrant.

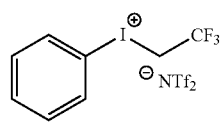

Notably, compared to its triflate analog, (CF$_3$SO$_3$)I(Ph)CH$_2$CF$_3$, the trifluoroethyliodonium triflimide salt 1 is more stable in ice-water, which is used in the last step of its preparation. Furthermore, the iodonium salt is a shelf-stable crystalline solid and represents an unusual example of a non-metallic single-component thiophile. This fact is especially important because earlier examples of single-component promoters, such as NBS (N-bromosuccinimide), possess a limited substrate scope. Lastly, it was anticipated that promoting glycosylations with 1 would not result in the formation of electrophilic byproducts, which is a problem with some thiophilic promoters.

Figure 5:
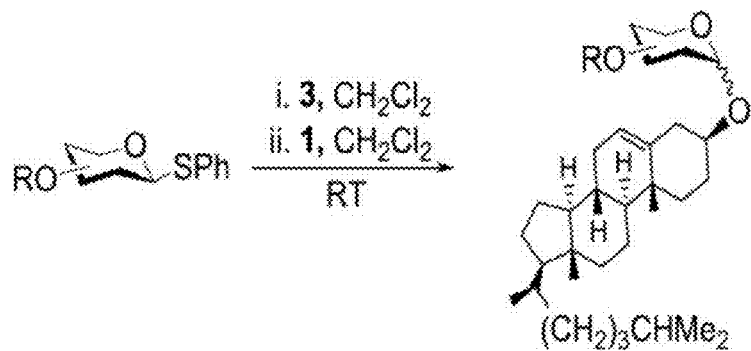
FIG. 5 is a table of glycosylation results using thiophilic promoter 1.

A preliminary study of the ability of compound 1 to promote glycosylation reactions employed fully armed glucose thioglycoside donor 2 and cholesterol (3) as coupling partners (FIG. 4). Dropwise addition of a solution of 1 (1.2 equiv.) in dichloromethane to a solution of the donor and acceptor at room temperature led to rapid formation (<20 min) of the desired glycosylation product in 63% yield (FIG. 5, entry 1). This result validated the hypothesis that promoter 1 can selectively react with thioglycosides in the presence of oxygen nucleophiles. With longer reaction times, however, complete product decomposition was observed (FIG. 5, entry 2). This was likely caused by acidic trifluomethanesulfonimide byproducts generated during the course of the reaction. Consistent with this rationale, the presence of non-nucleophilic base 2,4,6-tri-tert-butylpyrimidine (TTBP) in the reaction mixture prevented unwanted side-reactions, thereby improving the overall yield (FIG. 5, entry 3). Importantly, the effect of TTBP was not limited to donor 2, as the same phenomenon was observed with an array of different donor/acceptor pairs (FIG. 5, entry 4 vs. 5; entry 6 vs. 7). Therefore, these conditions were adopted for further studies.

Figure 6:
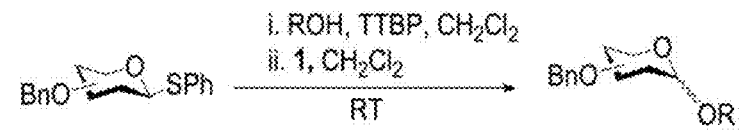
FIG. 6 is a table of substrate scope with armed thioglycoside donors.

As shown in FIG. 6, armed thioglycoside donors all reacted smoothly with various acceptors in consistently good yields (68% to 91%). Importantly, the use of sterically hindered acceptors does not negatively impact the overall efficiency of the reaction (FIG. 6, entry 3, 6, 9, and 12). Also worth noting is the overall trend of faster reaction times of fucose and galactose donors as compared to their glucose counterparts, which is consistent with previous reports of higher reactivities. We also showed that 6 is a competent donor in the reaction, demonstrating that the methodology can be applied to the synthesis of sensitive 2-deoxy-glycosides in excellent yields (FIG. 6, entries 10-12). Thus, the methodology is useful for the construction of natural product glycoconjugates (i.e., compounds comprising an aglycone moiety and a saccharide, such as glycoproteins, glycopeptides, glycosylated steroids, glycosylated polyene macrolide antibiotics, peptidoglycans, glycolipids, and lipopolysaccharides).

Figure 7:
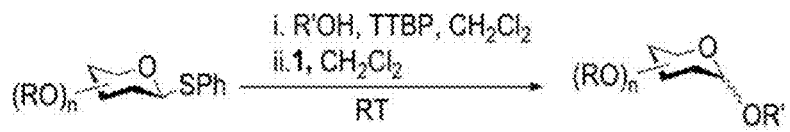
FIG. 7 is a table of substrate scope with disarmed thioglycoside donors.

In order to extend the substrate scope to include amino sugar donors, the use of 2-azido thioglycoside donor 7 was investigated in the glycosylation reaction. Despite bearing a highly disarming azide group on the neighboring C-2 position, glycosylations of 7 with all acceptors proceeded well (72% to 84% yield), albeit in longer reaction times (2 to 3.5 hours, FIG. 7, entries 1-3). Encouraged by this result, we next turned our attention to disarmed donors 8 and 9. Initial experiments revealed that products were obtained in modest yields (37% to 72% yield; FIG. 7, entries 4, 6, 8, and 10) as single anomers. Pleasingly, the yields could be significantly improved by reversing the donor acceptor stoichiometry (FIG. 7, entries 5, 7, 9, and 11). The effect is most apparent in the case of acceptor 10 and donor 8, where the yield was increased from 37% to 97% (FIG. 7, entry 6 vs. 7). Together with the results from FIG. 6, this study demonstrates that 1 is capable of activating both armed and disarmed thioglycoside donors at room temperature for subsequent glycosylations in a highly efficient and robust fashion.

Figure 8:
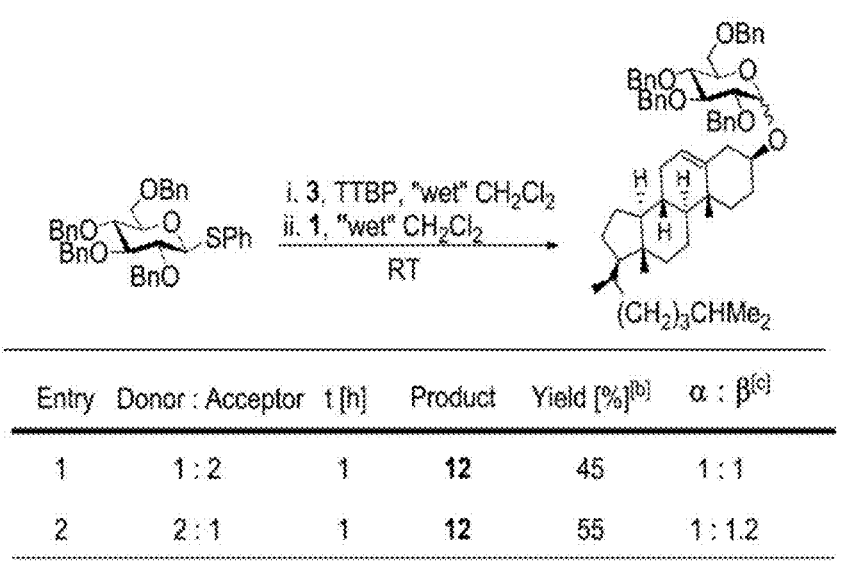
FIG. 8 is a table indicating the results of glycosylation reactions run under "wet" conditions.

A significant issue with many glycosylation protocols is that they are extremely water-sensitive, requiring stringent drying procedures. This requirement typically includes solvent drying and purification prior to the reaction, azeotropic drying of coupling partners, and the addition of molecular sieves to remove additional water. The water-stable characteristics of iodonium promoter 1 raised the possibility of carrying out a glycosylation reaction without pre-drying of the reagents. To this end, dichloromethane from previously opened solvent drums was used directly in the reaction, and the reaction was run open to the air. As shown in FIG. 8, an initial trial with these "wet" glycosylation conditions (i.e., conditions in which no effort was made to exclude air or moisture) demonstrated a 45% yield in the model reaction with similar anomeric selectivity as obtained in earlier experiments (compare FIG. 8, entry 1, and FIG. 6, entry 1). Importantly, no significant product decomposition was observed. Reversing the donor-to-acceptor ratio led to slightly increased yields (55%; FIG. 8, entry 2). Yields were lower under these conditions than when the solvents were pre-dried. Thus, our approach permits glycosylations between complex coupling partners without the need for rigorous drying of reagents and solvents beforehand. This fact greatly simplifies reaction setup, thereby laying the foundation for glycosylation protocols that can be used by the wider chemical biology community.

In conclusion, disclosed is the use of phenyl(trifluoroethyl) iodonium triflimide (1) as a representative of a new class of single-component thiophilic promoters. As a water/air-stable white crystalline solid capable of activating thioglycosides without any co-promoters, the iodonium salt offers significant advantages over other protocols stemming from its ease of use. The reaction is robust, and a wide array of both armed and disarmed thioglycoside donors were shown cleanly and rapidly to undergo glycosylation reactions in high yields at room temperature. In addition, rigorous drying of reagents and solvents was not necessary, further simplifying the reaction. Remarkably, this method will allow construction of carbohydrate libraries, and should impact glycomics in the same way that DNA synthesizers revolutionized genomics.

EXAMPLE 3

Effect of Nitrite Structure on Selectivity of Glycosylation Reaction

Figure 9:
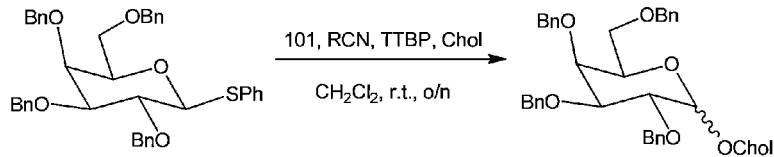
FIG. 9 tabulates the ratios of the anomeric configurations of the products obtained in glycosylations of cholesterol conducted at room temperature as a function of the identity of a nitrile additive.

It is well established that nitrile solvents can increase β-selectivity in glycosylation reactions. To our knowledge, there has been no report of a systematic survey of the effects of nitrile structure on selectivity. Schmidt, R. R. et al., *Synlett* 1990, 694-696. To this end, glycosylations promoted by the iodonium salts 101 and 102 were carried out in a number of different solvents. These studies showed that more electron-rich nitriles tended to provide higher levels of selectivity, while using electron-deficient nitriles led to decreased selectivity (FIG. 9).

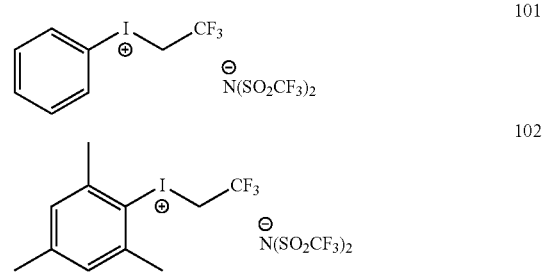

Figure 10:
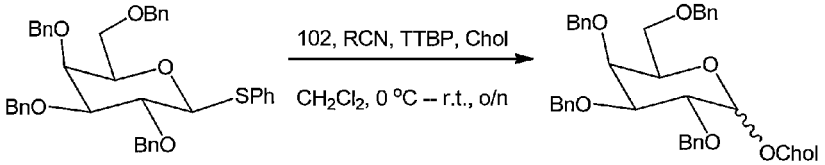
FIG. 10 tabulates the ratios of the anomeric configurations of the products obtained in glycosylations of cholesterol conducted at 0° C. as a function of the identity of a nitrile additive.

Furthermore, lowering the initial reaction temperature resulted in increased selectivity (FIG. 10).

EXAMPLE 4

Effect of Mixed Nitrite Solvents on Selectivity of Glycosylation Reaction

The use of mixed nitrile solvent systems was also examined. This resulted in a dramatic increase in selectivity, up to 25:1 β:α selectivity (FIG. 11). Remarkably, use of a combination of nitrile solvents results in a synergistic effect on the stereochemical outcome of a glycosylation reaction. This effect can be exploited with both primary and secondary nucleophilic acceptors. In most cases, a mixture of 1:1 pivalonitrile:isobutyronitrile or 1:1:1 isobutyronitrile:pivalonitrile:acetonitrile (IPA) gave the greatest selectivity (FIG. 12).

EXAMPLE 5

Methyl O-(2,3,4,6,-tetra-O-benzyl-D-glucopyranosyl)-(1->6)-2,3,4-tri-O-benzyl-α-D-glucopyranoside A reaction flask contained glycosyl donor (0.079 mmol), acceptor (0.158 mmol), and 2,4,6-Tri-tert-butylpyrimidine (TTBP, 0.158 mmol) dissolved in 4 mL dichloromethane and 1:1:1 mixture of acetonitrile/isobutyronitrile/pivalonitrile (0.3 mL of each nitrile, 0.9 mL in total). The reaction flask is then cooled to 0° C. in an ice-water bath.

Meanwhile, 1,3,5-Trimethylphenyl(trifluoroethyl)Iodonium triflimide (0.095 mmol) was separately dissolved with the identical 1:1:1 nitrile solvent mix as described above (0.3 mL of each nitrile, 0.9 mL in total). This solution was then added drop-wise to the reaction flask, and the reaction was allowed to stir in an ice bath overnight, while slowly warming up to room temperature.

Once the reaction was complete as indicated by TLC, it was quenched with triethylamine (Et$_3$N, 0.1 mL) and concentrated in vacuo. Flash column chromatography on silica gel afforded the desired product as determined by $^1$H and $^{13}$C NMR.

Data for major β-anomer:

$^1$H NMR (500 mHz, CDCl$_3$): δ 7.35-7.12 (m, 35H), 4.98 (d, J=4.6 Hz, 1H), 4.96 (d, J=4.4 Hz, 1H), 4.90 (d, J=10.9 Hz, 1H), 4.81-4.70 (m, 6H), 4.65 (d, J=12.1 Hz, 1H), 4.61-4.50 (m, 5H), 4.35 (d, J=7.8 Hz, 1H), 4.19-4.17 (m, 1H), 3.99 (t, J=9.2 Hz, 1H), 3.84-3.79 (m, 1H), 3.73-3.41 (m, 9H), 3.32 (s, 3H).

EQUIVALENTS

Those skilled in the art will appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. A method of preparing a compound represented by formula I:

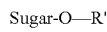

Sugar—O—R'     I comprising the step of combining R'—OH, a glycosyl donor of formula II, a reagent of formula III, and a base; wherein said base is selected from the group consisting of pyridine, pyrimidine, 2,6-lutidine, 2,6-di-tert-butylpyridine, 2,4,6-trimethylpyridine (collidine), diisopropylethylamine (DIPEA), 1,4-diazabicyclo [2.2.2]octane (DABCO), 1,8-Bis(dimethylamino)naphthalene (Proton Sponge), 1,8-diazabicyclo [5.4.0]undec-7-ene (DBU), and 2,4,6-tri-tert-butylpyridine (TTBP);

Sugar is an optionally protected monosaccharide or oligosaccharide;

O is an oxygen atom attached to an anomeric carbon atom of Sugar;

R' is selected from the group consisting of alkyl, haloalkyl, cycloalkyl, alkenyl, alkynyl, aryl, heteroaryl, aralkyl, heteroaralkyl, and heterocyclyl; or R'-OH is a steroid or an optionally protected monosaccharide, disaccharide, trisaccharide, tetrasaccharide, pentasaccharide, or hexasaccharide, wherein O is not bonded to an anomeric carbon atom of R';

formula II is represented by:

Sugar-S—R$^1$     II wherein

S is a sulfur atom attached to the anomeric carbon atom of Sugar;

R$^1$ is a phenyl, naphthyl, ethyl, or adamantyl group, each optionally substituted with one or more substituents independently selected from the group consisting of halo, alkyl, haloalkyl, perhaloalkyl, alkoxy, and cyano;

formula III is represented by:

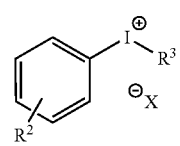

III wherein

R$^2$ is absent or represents one, two, or three substituents each independently selected from the group consisting of halo, alkyl, fluoroalkyl, perfluoroalkyl, alkoxy, cyano, acyl, and acyloxy;

R$^3$ is selected from the group consisting of fluoroalkyl, fluorohaloalkyl, and perfluoroalkyl; and X$^-$ is selected from the group consisting of boron tetrafluoride, tetraarylborate, tetra(fluoroaryl)borate, hexafluoroarsenate, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogen sulfate, alkyl sulfate, aryl sulfate, carbonate, bicarbonate, carboxylate, phosphate, hydrogen phosphate, and dihydrogen phosphate;

thereby forming the compound of formula I.

2. The method of claim 1, wherein Sugar is an optionally protected monosaccharide, disaccharide, or trisaccharide.

3. The method of claim 1, wherein Sugar is an optionally protected monosaccharide.

4. The method of claim 1, wherein Sugar is a protected glucopyranoside.

5. The method of claim 1, wherein R' is selected from the group consisting of alkyl, cycloalkyl, alkenyl, alkynyl, aralkyl, and heteroaralkyl; or R'—OH is a steroid or an optionally protected monosaccharide, disaccharide, trisaccharide, or tetrasaccharide.

6. The method of claim 1, wherein R'—OH is cholesterol.

7. The method of claim 1, wherein R'—OH is a protected monosaccharide or disaccharide.

8. The method of claim 1, wherein the OH group of R'—OH that forms a bond to the anomeric carbon atom of Sugar is the C3 or C6 hydroxyl of a protected monosaccharide or disaccharide.

9. The method of claim 1, wherein R'—OH is selected from the group consisting of

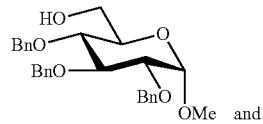

and

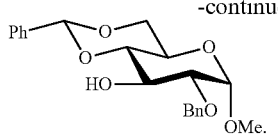

10. The method of claim 1, wherein $R^1$ is a phenyl or naphthyl group optionally substituted with one halo, alkyl, or haloalkyl.

11. The method of claim 1, wherein $R^1$ is an unsubstituted phenyl group.

12. The method of claim 1, wherein $R^2$ represents one or two substituents each independently selected from the group consisting of halo, alkyl, fluoroalkyl, and perfluoroalkyl.

13. The method of claim 1, wherein $R^2$ is absent.

14. The method of claim 1, wherein $R^3$ is fluoroalkyl.

15. The method of claim 1, wherein $R^3$ is 2,2,2-trifluoroethyl.

16. The method of claim 1, wherein $X^-$ is selected from the group consisting of methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, (trifluoromethanesulfonyl)(trifluoroacetyl)amide, and bis(p-toluenesulfonyl)amide.

17. The method of claim 1, wherein $X^-$ is selected from the group consisting of bis(methanesulfonyl)amide, bis(trifluoromethanesulfonyl)amide, bis(benzenesulfonyl)amide, and bis(p-toluenesulfonyl)amide.

18. The method of claim 1, wherein $X^-$ is bis(trifluoromethanesulfonyl)amide.

19. The method of claim 1, wherein the base is selected from the group consisting of pyridine, pyrimidine, 2,6-lutidine, 2,6-di-tert-butylpyridine, 2,4,6-trimethylpyridine (collidine), and 2,4,6-tri-tert-butylpyrimidine (TTBP).

20. The method of claim 1, wherein the base is 2,4,6-tri-tert-butylpyrimidine (TTBP).

21. The method of claim 1, wherein the glycosyl donor is selected from the group consisting of

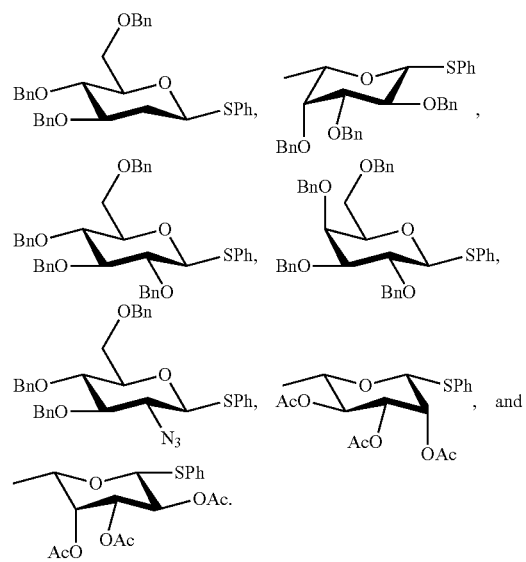

22. The method of claim 1, wherein the reagent of formula III is

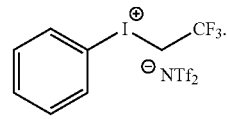

23. The method of claim 1, wherein Sugar is protected with one or more benzyl, para-methoxybenzyl, benzylidine, acetonide, methyl, acetyl, tert-butyloxycarbonyl, or silyl groups.

* * * * *